United States Patent [19]

Cox

[11] Patent Number: 5,558,100
[45] Date of Patent: Sep. 24, 1996

[54] BIOPSY FORCEPS FOR OBTAINING TISSUE SPECIMEN AND OPTIONALLY FOR COAGULATION

[75] Inventor: Dennis Cox, Saugus, Calif.

[73] Assignee: Ballard Medical Products, Draper, Utah

[21] Appl. No.: 358,899

[22] Filed: Dec. 19, 1994

[51] Int. Cl.$^6$ ............................................. A61B 10/00
[52] U.S. Cl. .................................. 128/751; 606/52
[58] Field of Search ......................... 128/751–754; 606/45, 46, 48, 49, 51, 52, 167, 170

[56] References Cited

U.S. PATENT DOCUMENTS

| | | | |
|---|---|---|---|
| 5,047,026 | 9/1991 | Rydell | 606/48 |
| 5,147,357 | 9/1992 | Rose et al. | 606/52 |
| 5,282,800 | 2/1994 | Foshee | 606/52 |
| 5,334,198 | 8/1994 | Hart et al. | 606/52 |
| 5,342,381 | 8/1994 | Tidemand | 606/52 |
| 5,373,854 | 12/1994 | Kolozsi | 606/52 |

FOREIGN PATENT DOCUMENTS

| | | | |
|---|---|---|---|
| 2573301 | 5/1986 | France | 606/52 |

*Primary Examiner*—Max Hindenburg
*Attorney, Agent, or Firm*—Workman Nydegger Seeley

[57] ABSTRACT

A biopsy forceps as disclosed that has a flexible hollow support cable with an insulating layer surrounding the support cable on its outer surface. An electrically conductive control wire extends through a central passage of the hollow support cable and has an insulating layer surrounding the portion of the control wire that is inside the support cable. The control wire is connected to an electrically conductive mount at a distal end of the control wire. The electrically conductive mount supports the pair of electrically conductive metal jaws which are pivotal and which have curved walls with sharp cutting edges which together form an enclosure for purposes of excising tissue. The control wire is electrically connected to a source of electrical current to permit selective energizing of the control wire as well as mechanical closing of the jaws when excising tissue, so as to provide simultaneous energizing of the mount, the pivotal jaws and also conductive spear for stabilizing and holding tissue that is positioned between the jaws.

4 Claims, 2 Drawing Sheets

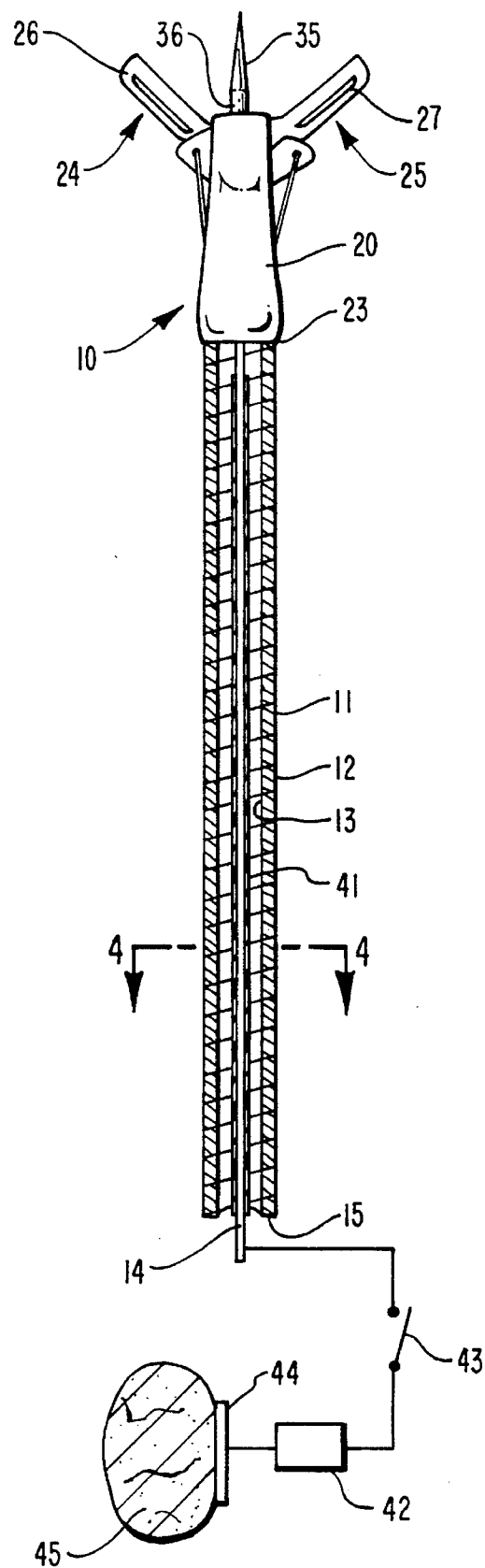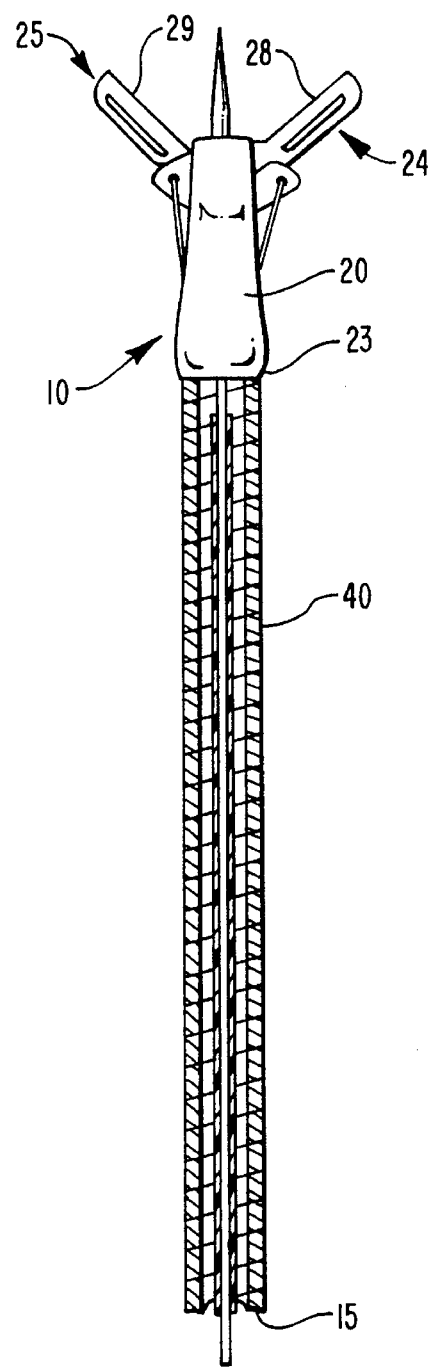
FIG. 1
FIG 2

BIOPSY FORCEPS FOR OBTAINING TISSUE SPECIMEN AND OPTIONALLY FOR COAGULATION

FIELD OF THE INVENTION

Biopsy forceps, especially for endoscopic procedures, which enable tissue samples to be cut and retrieved, and which can coagulate the incision if necessary, while still at the situs of the excision.

BACKGROUND OF THE INVENTION

Biopsy forceps, especially those which are intended for endoscopic use, provide a pair of mutually articulated jaws that can be opened at a situs where tissue is to be excised, and closed to cut and contain the specimen so it can be removed and examined. This is a routine procedure which rarely involves a complication. The wound is small and routinely heals.

However, the location of the situs always concealed from the surgeon, who must rely on telescopic or video means to observe the procedure, and occasionally a cut will be made through a vessel. In that event coagulation is necessary. In the prior art the forceps must be removed, and then coagulating means must be passed to the bleeding situs. The blood at the situs obscures the wound from being seen by any optical or video observation means. Locating the wound to be coagulated is both difficult and time-consuming, all to the disadvantage of the patient.

It is an object of this invention to enable the surgeon not only to excise the specimen, but also, if the cutting results in excessive bleeding, then without removing the forceps, to coagulate the wound. As a consequence, the coagulation occurs precisely where it is needed, and without delay to remove the forceps and to find and to place coagulating means where it is needed.

The problems of holding a specimen while it is being cut loose are well-known. When the forceps jaws are closed, the sample tends to slip before it is completely trapped. Then the desired tissue may not be caught. This problem has been addressed and solved in Bales U.S. Pat. No. 5,133,727, in which a pair of articulated jaws enclose a spear between them which impales the tissue and holds it in place while the jaws are closed to cut the specimen free.

It is an object of this invention to provide the stabilizing means shown in the Bales patent, and also to provide coagulating means to coagulate the wound while the forceps is still in place, if necessary. While this procedure sacrifices the specimen, it does attend to the wound, and leaves a clean field for a repeat effort to obtain a specimen.

BRIEF DESCRIPTION OF THE INVENTION

A forceps according to this invention includes a flexible support cable having a proximal and a distal end. The cable is flexible and tubular. It has an outer wall and an inner wall that forms a central passage.

A jaw mount is fastened to the support cable at its distal end. Two jaws are pivotally mounted to the jaw mount so as to open and close. They are provided with sharp cutting edges to form an enclosure which when the jaws are closed will retain a tissue specimen that the jaws cut loose when they were closed.

A control wire passes through the passage in the control cable, and is connected to the jaws so that reciprocating the control wire relative to the support cable will open and close the jaws.

A stabilizing spear is mounted to the mount. It extends into the enclosure. Its sharp point is directed between the jaws when they are open to spear a specimen to be excised.

According to this invention, the external wall of the support cable bears a layer of insulation to insulate it from the patient's body. The external wall of that portion of the control wire which is inside The support cable also bears a layer of insulation, thereby insulating the control wire from the support cable along that part of its length.

The control wire is electrically conductive, and is conductively connected to the jaws and because the jaws and the spear are metal and connected to one another, also to the spear.

Should coagulation be required, a high frequency burst of electrical energy is applied to the control wire and thus to the jaws. The patient himself is connected into the circuit, usually through a metal plate pressed against him. The resulting heat will coagulate the tissue which is in contact with the jaws and the spear.

The above and other features of this invention will be fully understood from the following detailed description and the accompanying drawing, in which:

BRIEF DESCRIPTION OF THE DRAWINGS

FIG. 1 is a side view, partly in axial cross-section, showing the preferred embodiment of the invention;

FIG. 2 is a back view of FIG. 1 also in partly in axial cross section;

DETAILED DESCRIPTION OF THE INVENTION

Figure 3:
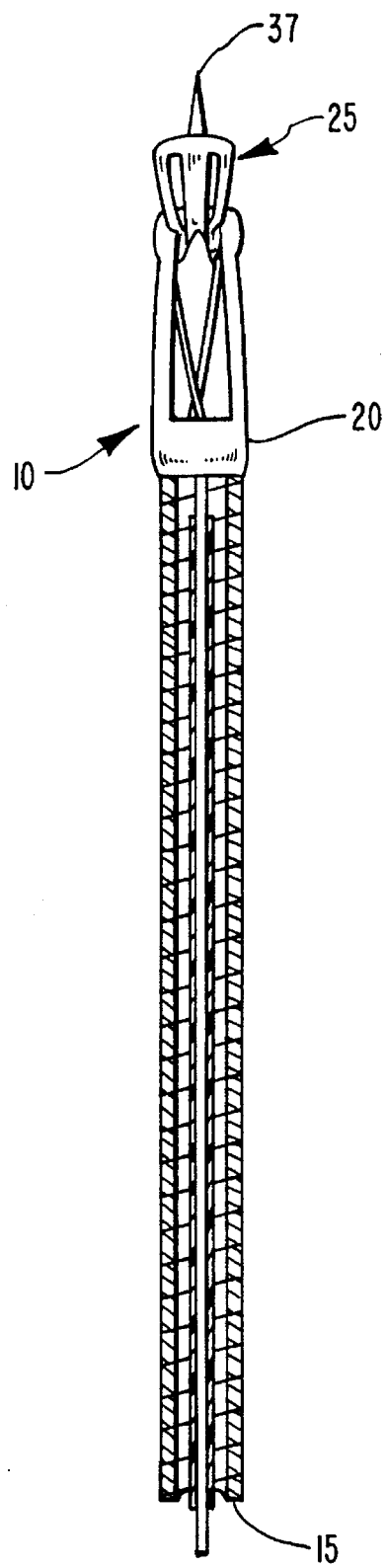
FIG. 3 is a right hard side view taken in FIG. 2, also partly in axial cross-section.
Figure 4:
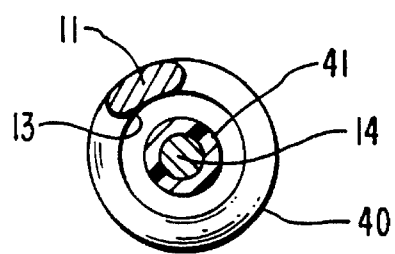
FIG. 4 is a cross section taken at line 4—4 in FIG. 1.

A forceps 10 according to this invention includes a flexible support cable 11. This cable is hollow. It conveniently is formed as a closely wound metal spring with convolutions 12 forming a central passage 13. A control wire 14 is slidingly fitted in passage 13.

The support cable has a proximal end 15 adapted to be attached to control means (not shown), such as a scissors type handle. The cable and the wire are attached to separate parts of the control means so the wire can be shifted axially in the passage.

A jaw mount 20 is attached to the distal end 23 of the cable. It supports electrically conductive jaws 24, 25, which are pivotally mounted to one another. There are various types of pivotal support for the jaws, of which this is merely one example. The important feature is that the jaws will be opened and closed relative to one another when the control wire is moved one way or the other.

Jaws 24, 25 have respective curved walls 26, 27 that have sharp edges 28, 29. When brought against or past one another they both cut and trap a tissue specimen in the enclosure 30 formed by them.

A metal stabilizing spear 35 is also mounted to the jaw mount. It has a shaft 36 with a pointed end 37 directed into the enclosure. When the forceps, with the jaws open, is pressed against the tissue to be excised, it stabs and stabilizes the tissue against lateral movement while the jaws make the cut.

As discussed this far, the arrangement is conventional. If the cut does not cause excessive bleeding such as by cutting a vein, nothing more is required. However, if such a cut is made, then without more the forceps must be removed, and a coagulator inserted. Then the search begins for the wound. It is a time-consuming and potentially difficult task.

According to this invention, a layer 40 of insulating material such as Teflon covers the outer wall of the support cable. It is conveniently applied as a tube and shrunk onto the support cable. It insulates the patient from the cable itself.

Further, a layer 41 of insulating material such as Teflon covers the outer wall of that part of the control wire which is in the passage. Again it can conveniently be applied as a tube and shrunk onto the control wire. This serves to insulate the length of the control wire from the support cable. As will be noted, the conductive mount and the control cable are in contact. However, the proximal end of the cable is not connected into the circuitry. The patient is insulated from the support cable.

A power supply 42 of conventional design, and a control switch 43 are connected to the control wire. A metal plate 44 against the patient 45 is connected to the power supply, thereby completing a path for the current whose effect is to coagulate tissue that is in contact with the jaws and the spear. After the coagulation is completed, the forceps will be withdrawn.

The tissue sample will have been sacrificed. However, the wound will have been coagulated, and a clean field remains for the next cut after the sample is removed and the forceps is again inserted.

Accordingly a forceps is provided which in addition to its cutting and stabilizing features is provided with coagulating means available for use immediately at the cutting situs should it be needed.

This invention is not to be limited by the embodiment shown in the drawings and described in the description, which is given by way of example and not of limitation, but only in accordance with the scope of the appended claims.

I claim:

1. A biopsy forceps apparatus comprising: a flexible hollow support cable with a proximal end, having a distal end and a central passage from end to end, said support cable having an insulating layer surrounding an outer surface of the support cable from end to end;

a single electrically conductive control wire slidably fitted in and extending through said central passage, said electrically conductive control wire having an insulating layer surrounding that portion of the control wire which is inside said support cable and being connected to an electrically conductive mount at a distal end of the control wire;

an electrically conductive mount connected to said support cable at the distal end thereof, and comprising means for pivotally supporting a pair of electrically conductive metal jaws at the distal end of said support cable, said jaws having curved walls with sharp cutting edges which together form an enclosure when closed to trap an excised tissue specimen;

an electrically conductive spear means for stabilizing and holding tissue to be excised by said jaw, said spear means connected to said mount at the distal end of said support cable, and having a shaft with a pointed end extending into the enclosure formed by said jaws as they are closed to excise tissue; and means for connection of said electrically conductive control wire to a source of electrical current so as to permit selective energizing of said control wire or mechanical closing of said jaws to excise tissue, and thereby simultaneous energizing of the mount, jaws and spear means;

whereby tissue can be either excised or cauterized by said apparatus, as selected by a user.

2. A biopsy forceps according to claim 1 in which said cable is a flexible tightly wound helical spring.

3. A biopsy forceps according to claim 1 in which said insulator means are tubes of insulative material shrunk onto the support cable and onto the control wire.

4. In combination:

a biopsy forceps according to claim 1, a power supply for electrical current, switch means interconnecting said control wire at its proximal end to said supply, and a conductive plate connected to said power supply for attachment to a patient in whom a biopsy is to be performed.

* * * * *

UNITED STATES PATENT AND TRADEMARK OFFICE
CERTIFICATE OF CORRECTION

PATENT NO. : 5,558,100

DATED : September 24, 1996

INVENTOR(S) : Dennis Cox

It is certified that error appears in the above-indentified patent and that said Letters Patent is hereby corrected as shown below:

Column 2, line 11, "The" should be --the--.
Column 3, line 45, delete "having".
Column 4, line 19, "jaw" should be --jaws--.

Signed and Sealed this

Twenty-second Day of July, 1997

Attest:

BRUCE LEHMAN

Attesting Officer

Commissioner of Patents and Trademarks